(12) United States Patent
Waldenburg

(10) Patent No.: US 6,692,468 B1
(45) Date of Patent: *Feb. 17, 2004

(54) DUAL-CHAMBER SYRINGE AND METHODS

(76) Inventor: Ottfried Waldenburg, 8424 E. Amethyst La., Tucson, AZ (US) 85750

( * ) Notice: Subject to any disclaimer, the term of this patent is extended or adjusted under 35 U.S.C. 154(b) by 0 days.

This patent is subject to a terminal disclaimer.

(21) Appl. No.: 09/562,411

(22) Filed: May 1, 2000

Related U.S. Application Data

(63) Continuation-in-part of application No. 08/312,878, filed on Sep. 27, 1994, now Pat. No. 5,496,284.

(51) Int. Cl.[7] .............................................. A61M 5/00
(52) U.S. Cl. ........................ 604/191; 604/89; 604/91; 604/218; 604/246
(58) Field of Search ............................. 604/89, 91, 92, 604/181, 183, 184, 187, 191, 218, 246

(56) References Cited

U.S. PATENT DOCUMENTS 5,078,691 A * 1/1992 Hamacher .................. 604/183
5,496,284 A * 3/1996 Waldenburg ............... 604/191
6,132,400 A * 10/2000 Waldenburg ............... 604/191

FOREIGN PATENT DOCUMENTS

DE 554894 * 7/1932

* cited by examiner

Primary Examiner—Brian L. Casler
Assistant Examiner—Jeremy Thissell
(74) Attorney, Agent, or Firm—John J. Connors; Connors & Associates, Inc.

(57) ABSTRACT

A dual-chamber syringe has a plunger within an inner delivery chamber in fluid communication with an ejection port. The deliver chamber is formed within a tubular element axially slidable within a tubular guide. The tubular guide and the syringe outer barrel form an outer reservoir chamber. The outer reservoir chamber is sealed from the delivery chamber while the tubular element is in a first position within the guide. Upon withdrawal of the plunger, frictional contact imparted by the plunger seal causes the tubular element to slide away from sealing engagement with the barrel into a second position within the guide. In the second position of the tubular element, a fluid passageway is opened from the reservoir to the delivery chamber allowing fluid to be drawn into the delivery chamber. A porous seal between the plunger rod and barrel allows air into the reservoir during transfer of fluid to the delivery chamber. Pressing the plunger inward first moves the tubular element from the second position back to the first position to close the fluid passageway and then expels fluid from the delivery chamber through the ejection port.

5 Claims, 9 Drawing Sheets

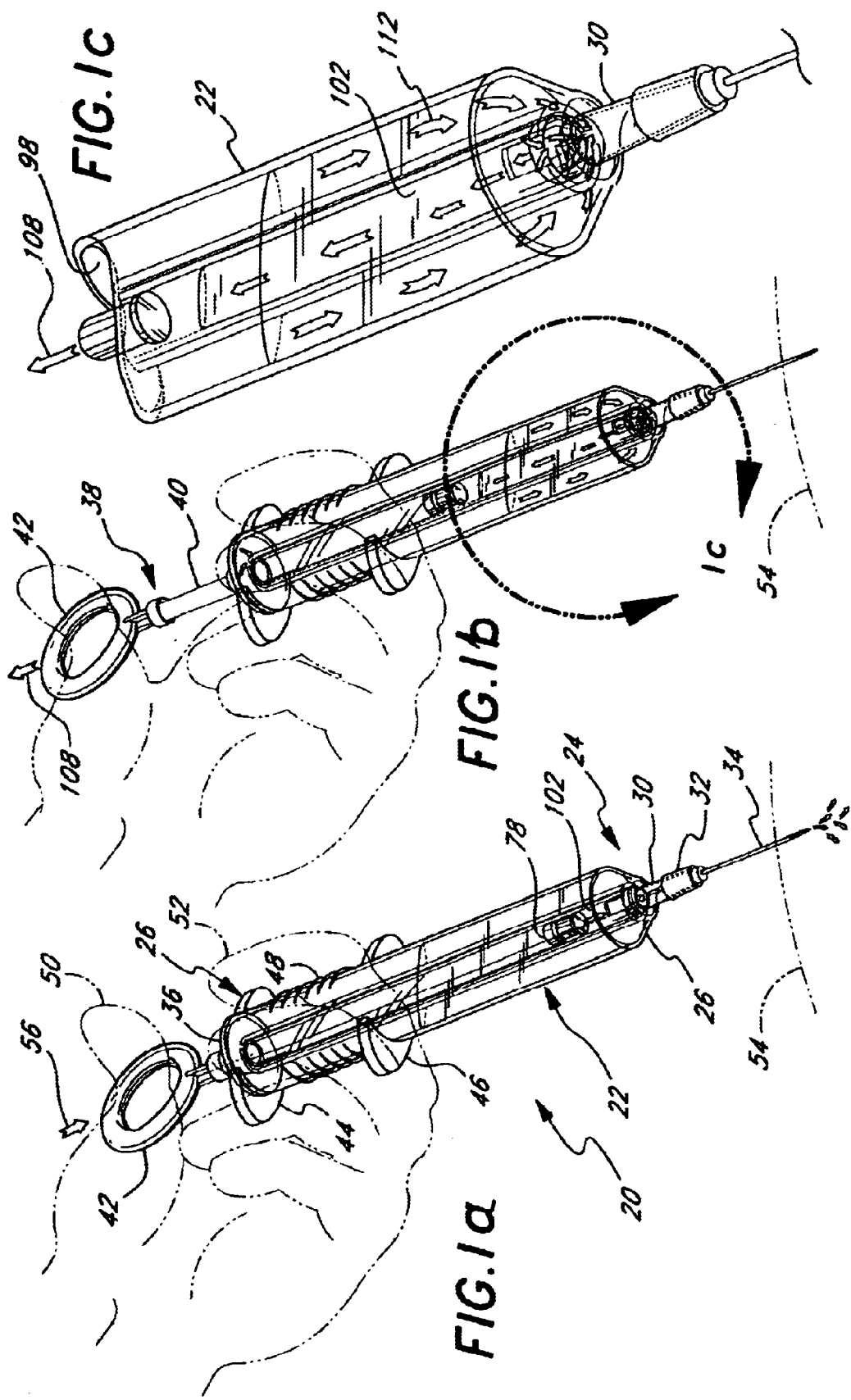

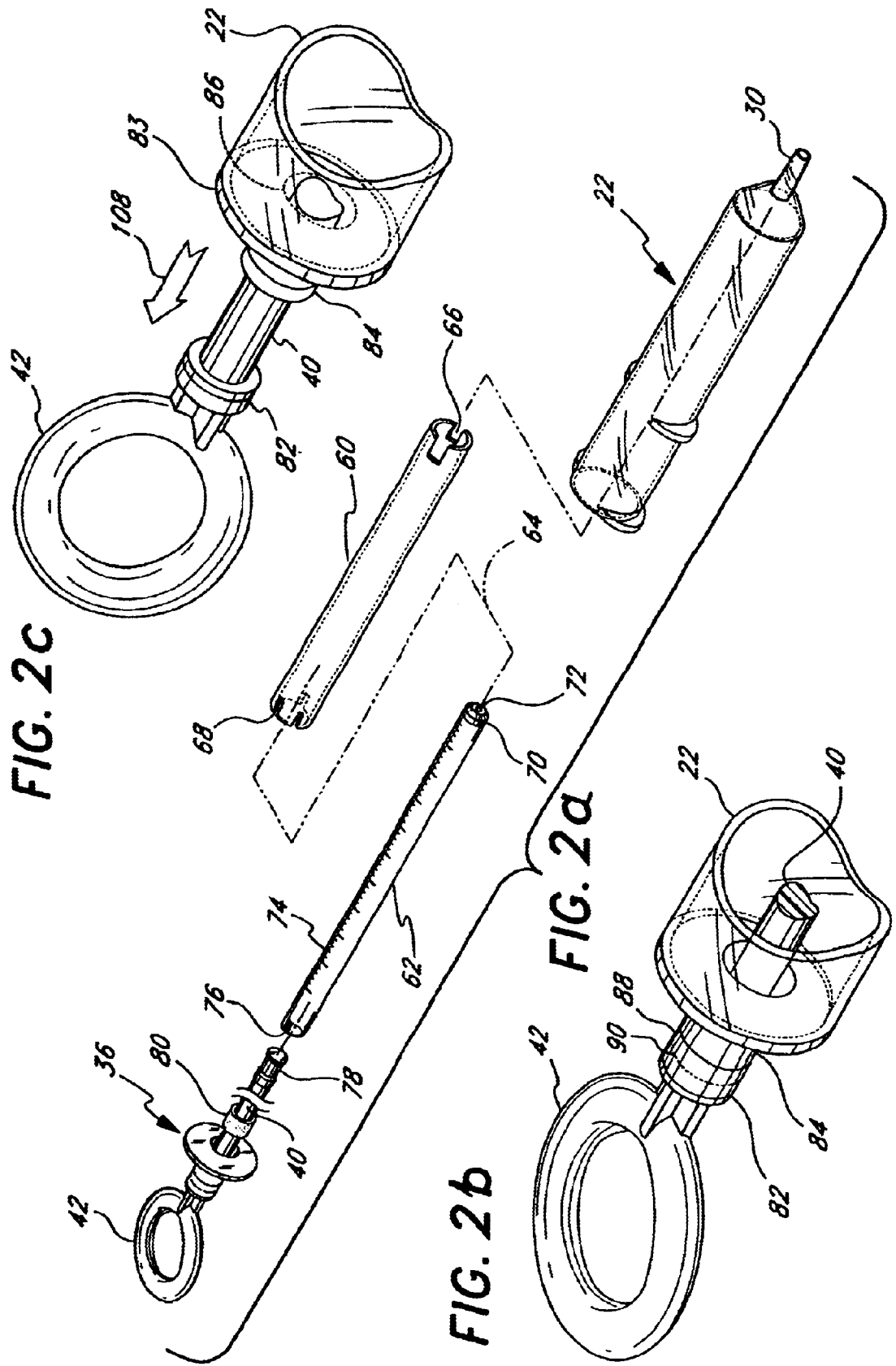

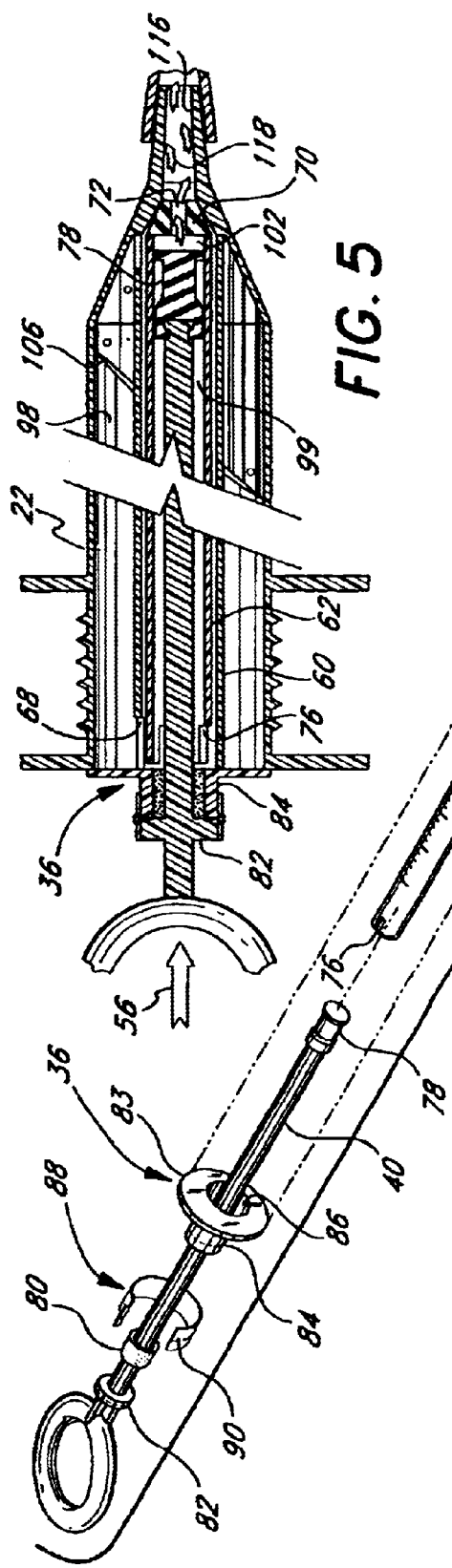
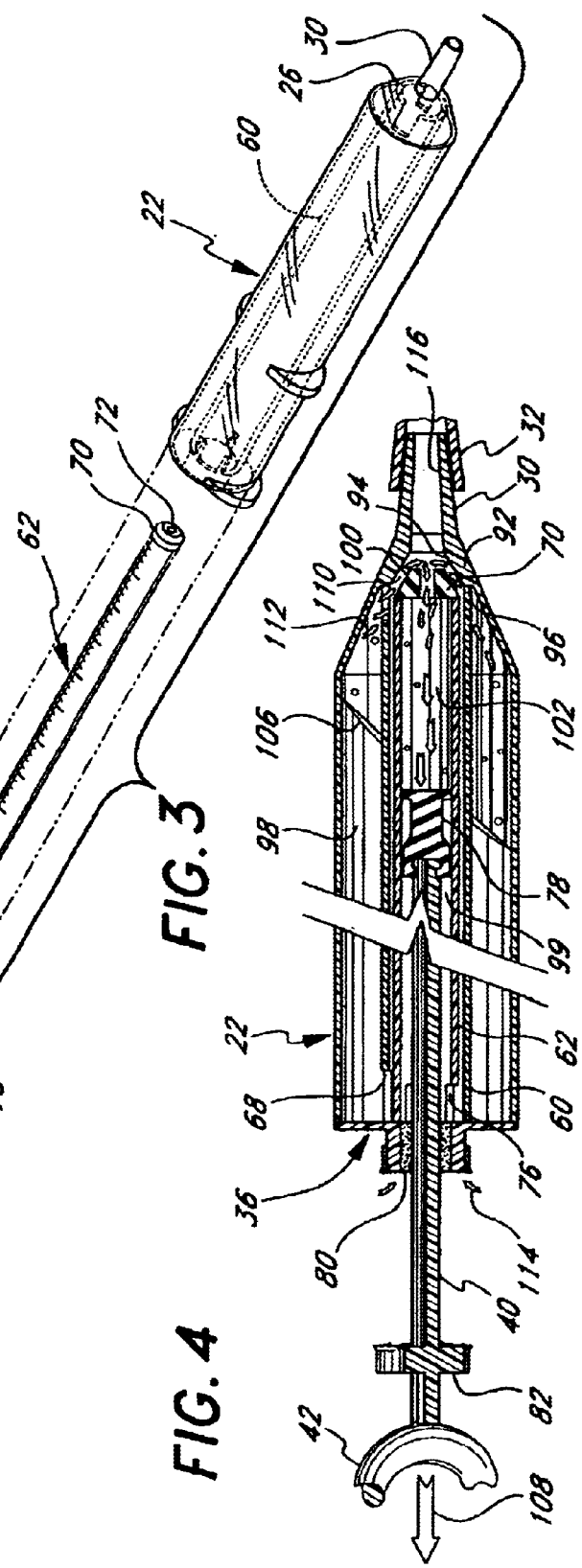

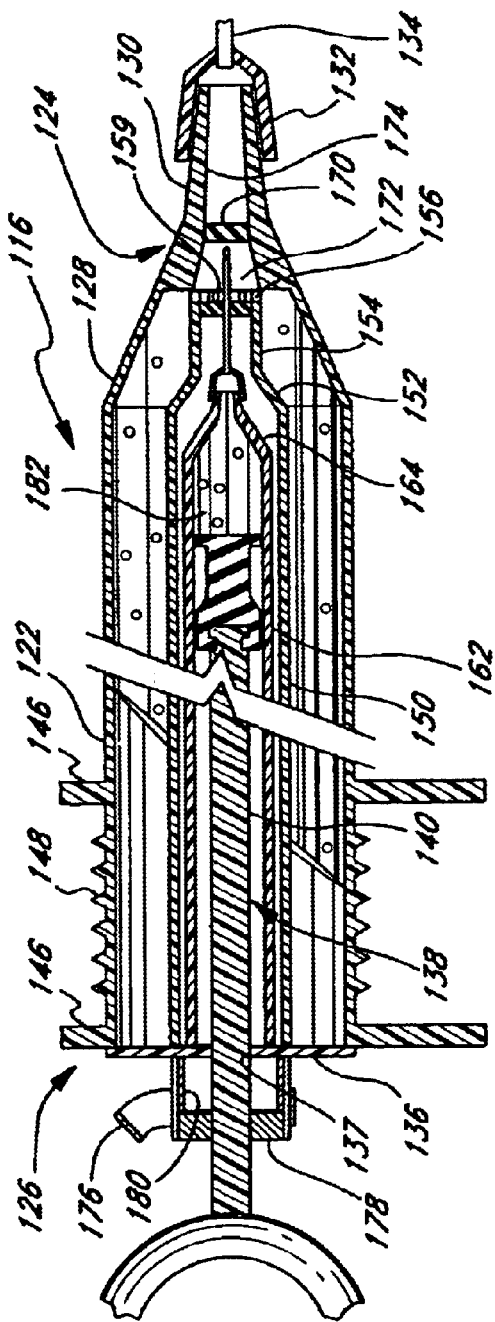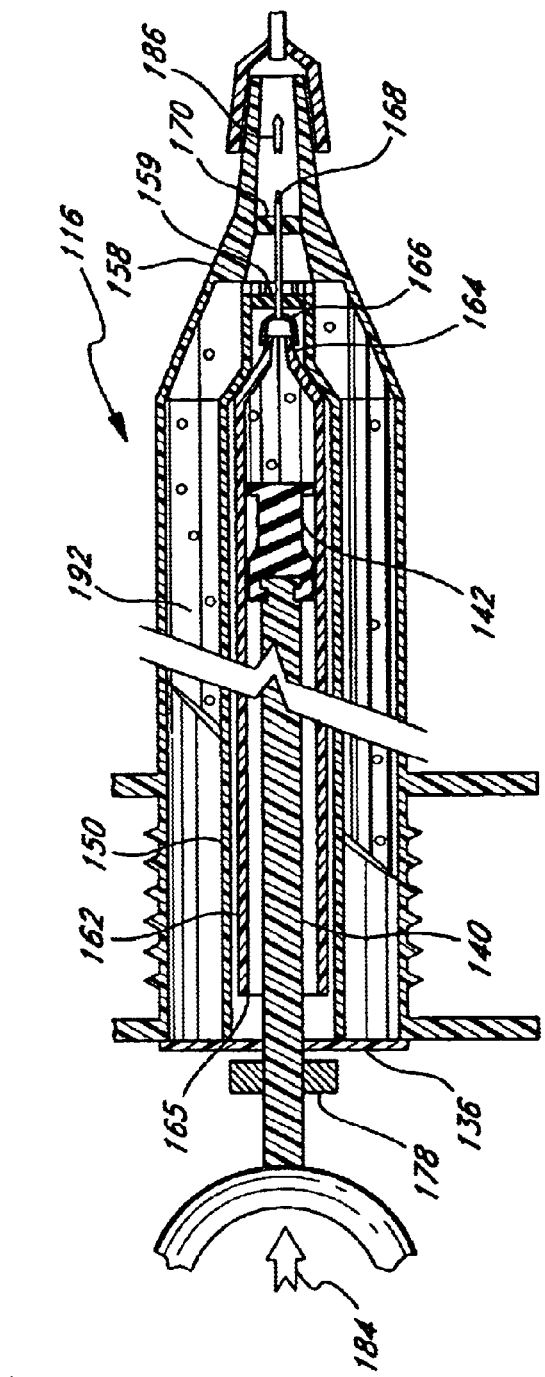
FIG. 6
FIG. 7

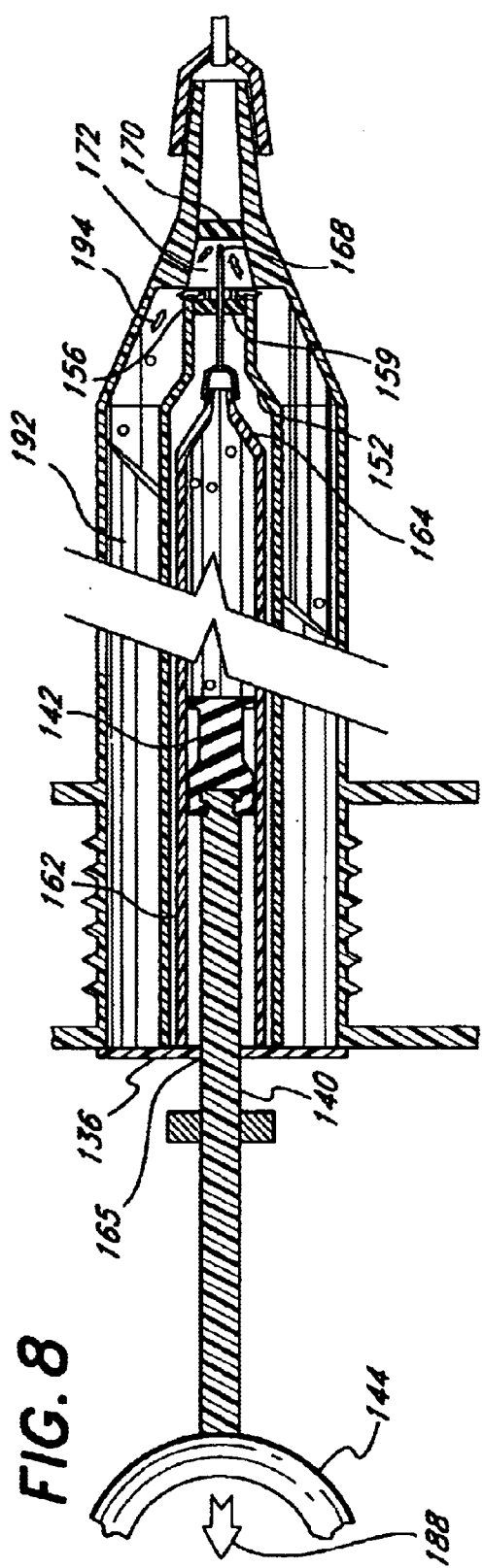
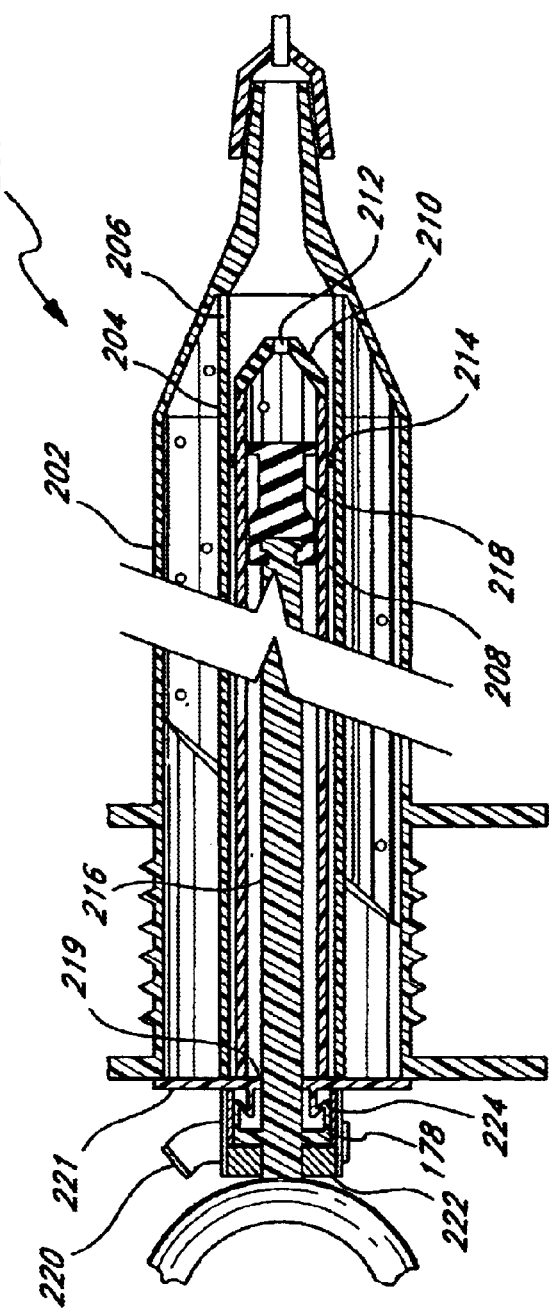
FIG. 8
FIG. 9

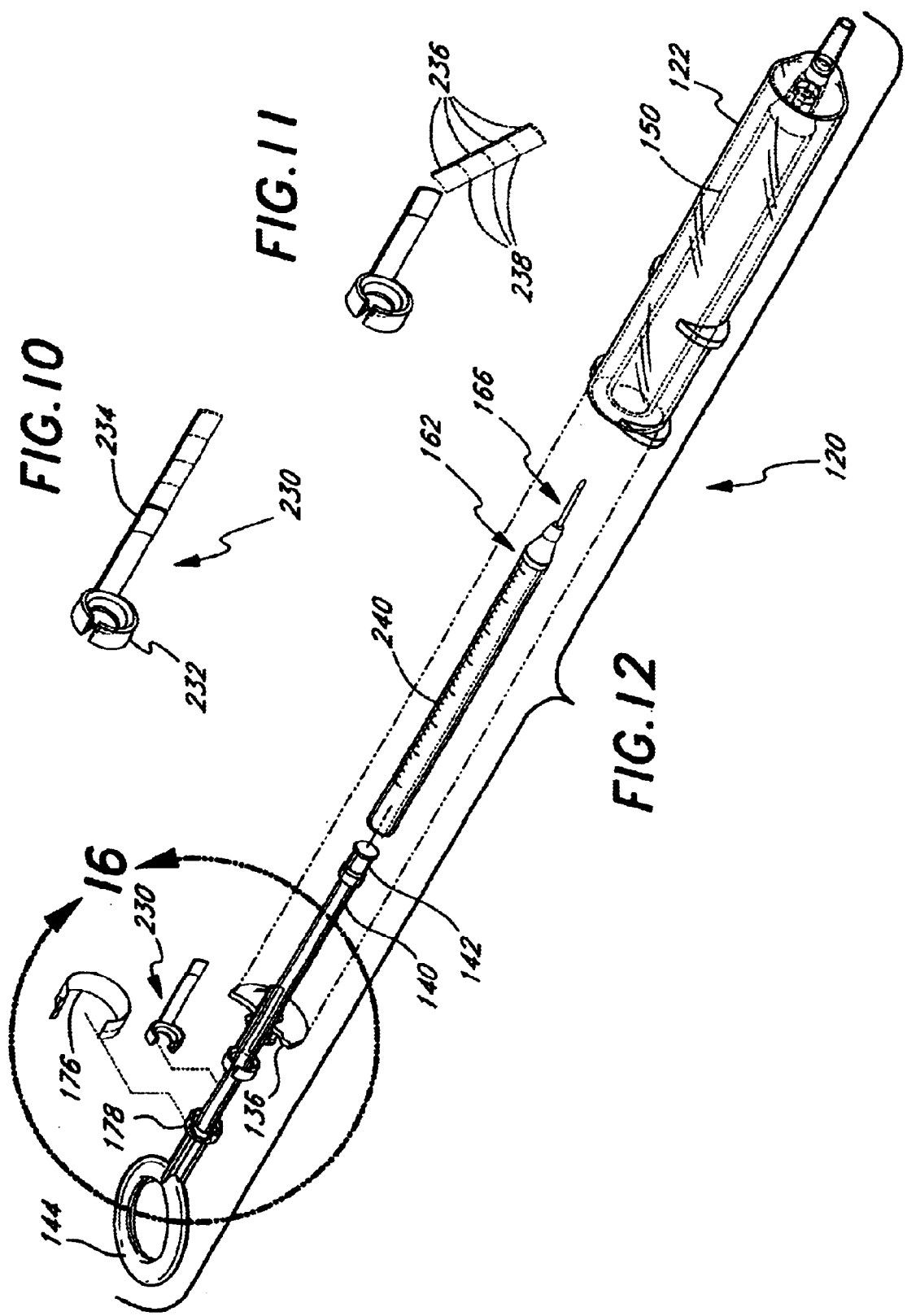

DUAL-CHAMBER SYRINGE AND METHODS

RELATED PATENT APPLICATIONS

This application is a continuation-in-part application of U.S. Ser. No. 08/312,878, entitled "Dual-Chamber Syringe & Method," filed Sep. 27, 1994, now U.S. Pat. No. 5,496,284, which is incorporated herein by reference and made a part of this application.

BACKGROUND OF THE INVENTION

1. Field of the Invention

This invention relates to an improved syringe and, more particularly, to a dual-chambered syringe having a fluid reservoir accessible to a delivery chamber upon axial displacement of a plunger.

2. Background Discussion

In many medical procedures there is a need for locally anesthetizing a large region subject to an operation or other treatment. Local administration of anesthetic may require several distinct injections in the affected area, or injection of a first volume of anesthetic at a relatively shallow depth followed by one or more further injections after advancing the hypodermic needle deeper into the tissue of the patient, or both. This successive delivery of anesthetic to varying tissue depths ensures a complete and measured numbing of all of the nerve endings in the treated region.

When delivering a large quantity of any fluid using a syringe, such as in the successive, varying depth injection method, the syringe must have a large capacity, or must be withdrawn intermittently and refilled. Large syringes are cumbersome, and it is often difficult to meter small quantities with them as the barrel has a large cross-section. Thus, even a small movement of the plunger correlates to a large fluid displacement. Even smaller syringes having volumetric graduations used to inject two or three sequential doses are difficult to meter exactly. Moreover, the smaller the diameter of the syringe, the less pressure is required to deliver the injection, and consequently, less pain. Withdrawal of the syringe from an injection site for refilling and subsequent re-injection is inconvenient and increases the chance of infection and trauma to the patient.

There have been efforts in the prior art to provide a dual-chamber syringe for storing a volume of fluid in a reservoir to be transferred into a delivery chamber, or visa versa. Typically, the fluid is ejected from the delivery chamber through a nozzle by a plunger. There are various motivations for providing dual-chamber syringes, including simply increasing the syringe capacity, providing a sterile self-contained single-use syringe, and mixing two components prior to injection, for example. Many of the known devices, however, require the injection nozzle to be plugged prior to transferring fluid between the reservoir and the delivery chamber. In other known devices, one chamber is placed in communication with another only upon relative rotation of the chamber barrels.

One dual-chamber syringe is shown in U.S. Pat. No. 553,234 issued to Finot. This syringe includes a rotatable inner chamber for selectively communicating the inner chamber with either the injection nozzle or the reservoir. Despite the benefit of a larger carrying capacity, the syringe must be manipulated with two hands to transfer fluid between chambers. Further, the syringe of Finot was not designed for successive, varying depth injections which are best accomplished rapidly and with minimum lateral movement.

Despite numerous previous dual-chamber syringe designs, all share the drawback of requiring a two-handed operation to transfer fluid between the internal chambers. There is thus a need for a dual-chamber syringe particularly suited for successive, varying depth injections which can be actuated with one hand.

SUMMARY OF THE INVENTION

The syringe of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include one-handed operation; convenience of use; larger capacity; successive, varying depth injection of anesthetic; ease of introduction of medication into dense tissue; better control of quantity of anesthetic used, thereby avoiding unnecessary tissue swelling; filtration of air introduced into syringe; the use of a single needle to give multiple injections without the need to remove the needle from the body of the patient; reduction of pain during injection because smaller diameter needles may be used; and elimination of vials holding medication, thereby reducing of likelihood contamination.

The first feature of the medical syringe of this invention is that it includes a plunger having at one end a resilient seal, and a barrel having a central longitudinal axis and a pair of opposed ends. The plunger has at an end remote from the end with the resilient seal thereon a thumb ring, and the barrel has at least one external finger rest. The barrel has at one end an ejection port and at the other end an opening. Preferably, the opening in the barrel has a porous seal which surrounds the plunger. This porous seal allows air to enter the barrel yet inhibits the flow of liquid from the chamber. The ejection port and opening are aligned with each other and disposed along the longitudinal axis.

The second feature is outer and inner telescopic tubular elements seated inside the barrel to be coaxial with the longitudinal axis. The outer tubular element is mounted in a stationary position while disposed in the barrel and the inner tubular element is movable axially within the outer tubular element. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon.

The third feature is that the resilient seal fits snug within the inner tubular element to grip the inner tubular element. In response to axial movement of the plunger, the inner tubular element is moved between a first and second positions. In the first position, the seal with the orifice therein seals the injection port as the plunger is moved towards the injection port, preventing liquid in the chamber from passing into the inner tubular element and forcing any liquid in the inner tubular element through the orifice and out the injection port. In the second position, the seal with the orifice therein is moved to a retracted position away from the injection port, allowing liquid to flow from the chamber through the passageway and through the orifice into the inner tubular member.

The fourth feature is that the plunger is initially in a forward position that forces the seal with the orifice therein into engagement with the injection port to seal this port. Preferably, there is a safety seal on the plunger which is broken by movement of the plunger into a retracted position, pulling the seal with the orifice therein away from the injection port. This thereby initially fills the inner tubular element with liquid from the chamber. preferably, the barrel and inner and outer tubular elements are made of a transparent or translucent material.

In another embodiment of this invention, a back flow seal is disposed in the ejection port preventing fluid from entering or leaving said barrel through said ejection port. The back flow seal forms a distal boundary of a refill chamber within said barrel. In this embodiment, the inner tubular element has at its distal end a needle having a distal tip. In response to axial movement of the plunger, the inner tubular element moves between a first position where said distal tip of the needle is located within said refill chamber allowing fluid to be drawn through the distal tip into the inner tubular element by proximal movement of the plunger relative to the inner tubular element, and a second position where said distal tip extends through said back flow seal into the ejection port allowing fluid to be expelled through said ejection port upon distal movement of the plunger relative to the inner tubular element. Preferably, there is a safety seal on the plunger which must be broken before the plunger may move with respect to the barrel.

This invention also includes a method of giving an injection of an anesthetic into the body of a patient. This method includes the steps of (a) providing a syringe with a reservoir that contains the anesthetic and a delivery channel which receives a plunger which when moved in one direction places the channel in communication with the reservoir and in another direction discontinues the communication and ejects anesthetic from the channel, (b) initially introducing the anesthetic using the syringe into the body of the patient, and (c) introducing a second dosage of the anesthetic by moving the plunger in the one direction to place the reservoir into communication with the channel and refill the channel with anesthetic and then moving the plunger in the other direction to discontinue the communication and eject anesthetic from the channel.

This invention also includes a method of giving of a medication into the body of a patient, including the steps of (a) providing a syringe with a reservoir that contains the medication and an inner tube defining a delivery channel, said tube having a needle on one end and a plunger received in the opposite end, said plunger placing the needle in communication with the reservoir when moved in one direction and discontinuing the communication and ejecting medication from the channel when moved in another direction, and (b) using the syringe initially to introduce the medication into the body of the patient, and (c) introducing a second dosage of the medication by moving the plunger in the one direction to place the reservoir into communication with the needle and refill the channel with medication and then moving the plunger in the other direction to discontinue the communication and eject medication from the channel.

This invention also includes a method of injecting fluid from a syringe, including the steps of withdrawing a plunger to displace an inner tubular element into a first position within said syringe, said tubular element having a needle thereon, the needle reversing out of a back flow seal mounted in an ejection port by movement of the tubular element into said first position, withdrawing said plunger to displace an inner resilient seal with respect to the tubular element creating a reduced pressure within said tubular element and drawing fluid therein through said needle from a reservoir formed outside of said tubular element, depressing said plunger to displace the inner tubular element into a second position within said syringe, said needle piercing said back flow seal to reach said ejection port by movement of the tubular element into said second position, and depressing said plunger to displace said inner resilient seal with respect to the tubular element creating an elevated pressure within said tubular element and expelling fluid therein through said needle into said ejection port.

In these methods only one hand is used to manipulate the syringe.

DESCRIPTION OF THE DRAWING

The preferred embodiment of this invention, illustrating all its features, will now be discussed in detail. This embodiment depicts the novel and non-obvious syringe and methods of this invention as shown in the accompanying drawing, which is for illustrative purposes only. This drawing includes the following figures (Figures), with like numerals indicating like parts:

FIG. 1a is a perspective view of a dual-chamber syringe of the present invention during delivery of fluid to an injection site through a needle.

FIG. 1b is a perspective view of the dual-chamber syringe of FIG. 1 during transfer of a fluid from an internal reservoir to a delivery chamber.

FIG. 1c is an enlarged perspective view of a distal end of the syringe in FIG. 1b showing fluid flow from the reservoir into the delivery chamber.

FIG. 2a is an exploded, perspective view of the dual-chamber syringe of FIG. 1 showing the components of the syringe.

FIG. 2b is an enlarged perspective view of a proximal end of the dual-chamber syringe of FIG. 1 prior to rupture of a safety seal;

FIG. 2c is an enlarged perspective view similar to FIG. 2b after the safety seal has been ruptured;

FIG. 3 is another exploded, perspective view of the syringe of FIG. 1 showing the components of the syringe.

FIG. 4 is a cross-sectional view of the syringe of FIG. 1 during transfer of fluid from an internal reservoir to a delivery chamber.

FIG. 5 is a cross-sectional view of the syringe of FIG. 1 during delivery of a fluid through an ejection port.

FIG. 6 is a cross-sectional view of an alternative embodiment of a dual-chamber syringe of the present invention prior to an initial use thereof.

FIG. 7 is a cross-sectional view of the syringe of FIG. 6 during delivery of a fluid through an ejection port.

FIG. 8 is a cross-sectional view of the syringe of FIG. 6 during transfer of fluid from an internal reservoir to a delivery chamber.

FIG. 9 is a cross-sectional view of a further embodiment of a dual-chamber syringe prior to an initial use thereof.

FIG. 10 is a perspective view of a whole calibrated dose meter for use with the dual-chamber syringe of FIG. 6.

FIG. 11 is a perspective view of the dose meter of FIG. 10 with several calibrated segments broken away.

FIG. 12 is an exploded, perspective view of a further embodiment of a dual-chamber syringe adapted to be used In conjunction with the dose meter of FIG. 10.

DETAILED DESCRIPTION OF THE PREFERRED EMBODIMENTS

Figure 13:
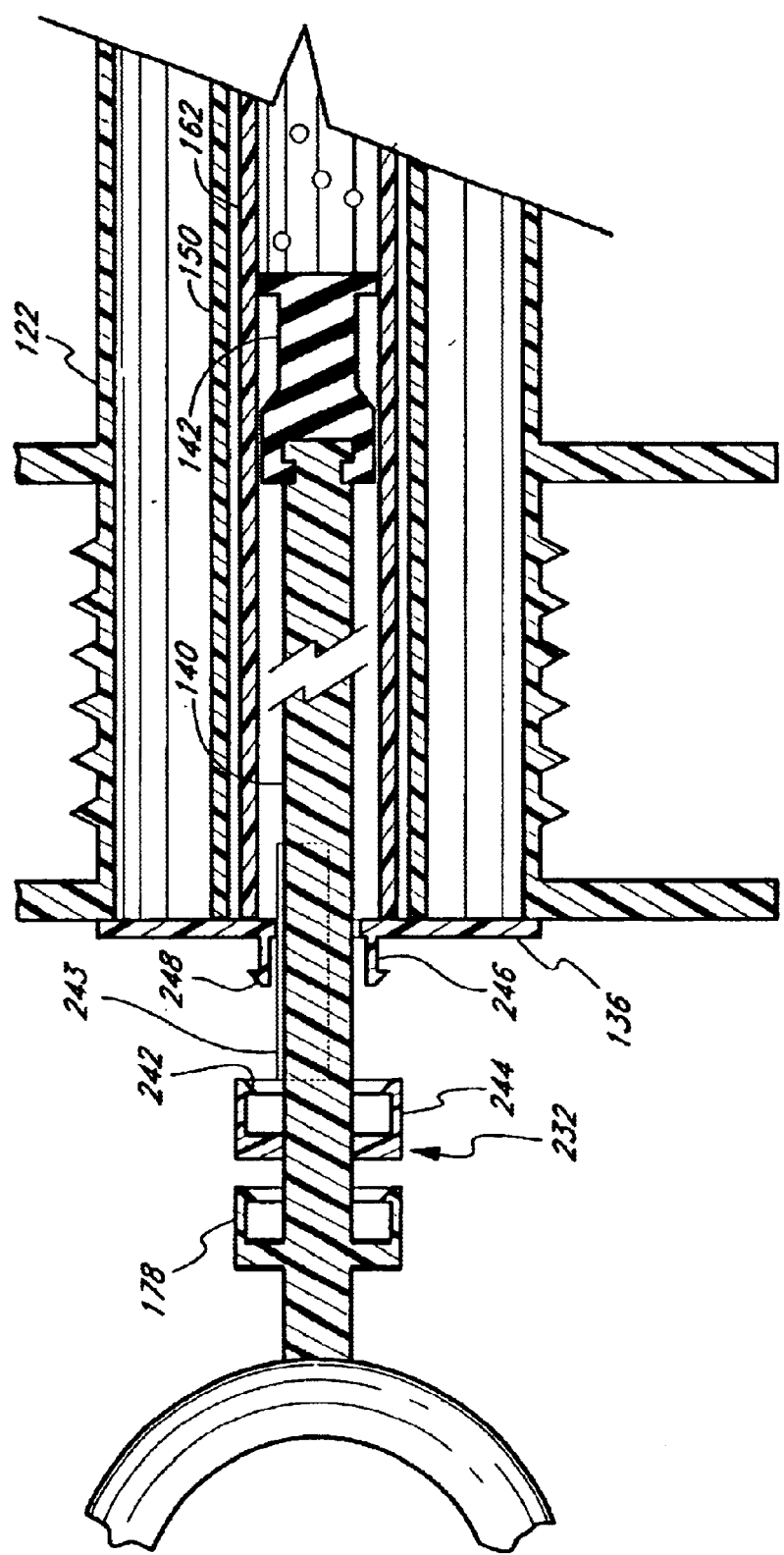
FIG. 13 is a detailed, cross-sectional view of the syringe of FIG. 12 prior to installation of the dose meter.

As shown in FIG. 1a, a first embodiment of a dual-chamber medical syringe 20 includes an outer tubular barrel 22 including a distal end 24 and a proximal end 26. The distal end 24 includes a tapered section 28 leading to a stem 30 for receiving a hub 32 of a needle 34. Those skilled in the art will understand that the stem 30 is of a generally standard type in the medical industry, and various needles and the like will be readily received thereon.

The proximal end 26 of the barrel 22 is covered by an end cap 36 having an aperture 86 (FIG. 3) for receiving a plunger 38. The plunger 38 includes a plunger rod 40, as seen in FIG. 1b, and a thumb ring 42 on its proximal end. The barrel 22 further includes a first pair of outwardly extending finger rests 44 adjacent to the end cap 36 and a second pair of outwardly extending finger rests 46 proximally disposed with respect to the first pair. Additionally, a series of external circumferential grip ribs 48 are formed on the barrel 22 between the finger rests 44, 46.

The syringe 20 is thus configured to allow a medical technician to insert a thumb 50 through the thumb ring 42 while gripping the barrel 22 with the index and middle fingers 52 in the general location of the ribs 48. The syringe 20 exhibits both finger rests 44 and 46 to allow an operator to displace the thumb ring 42, and associated plunger rod 40, in either axial direction with respect to the barrel 22. FIG. 1a shows the needle 34 after having pierced an injection site 54. Movement of the plunger 38 in the direction of arrow 56 relative to the barrel 22 forces fluid out of the needle 34, as shown by arrows 58. Advantageously, this one-handed operation facilitates rapid and steady, successive, varying depth injections, as will be more fully explained below.

Looking now at FIG. 2a, the cylindrical barrel 22 is sized to receive a channel member or tubular guide 60 which, in turn, receives a tubular element 62. When assembled, the three tubular elements 22, 60 and 62 fit concentrically within one another along a common longitudinal axis 64. The tubular guide 60 is slightly longer than the tubular element 62. When assembled, as shown in FIG. 4, the proximal end of the guide member 60 contacts the end cap 36, and distal end abuts the tapered section 28. The tubular element 62, on the other hand, is free to slide axially within the guide member 60 a short distance, the reason for which will be explained further below.

The tubular guide 60 includes a pair of diametrically opposed axial slots 66 in the distal end and a plurality of axial slots 68 in the proximal end. The tubular element 62 is fitted with an elastomeric, plunger-like seal 70 on its distal end having an orifice 72 therethrough. A large portion of the tubular element 62 is marked with a series of volumetric graduations 74. A breather slot 76 is formed in the distal end of the tubular element 62.

The plunger 38, as shown exploded in FIG. 3, includes a resilient fluid seal 78 attached to the distal end. A porous sleeve or seal 80 fits snugly around the plunger rod 40 intermediate the seal 78 and a stop ring 82. The end cap 36 is defined by a flat disk portion 83 sized to cover the proximal end of the barrel 22 and a circular flange 84 extending in a proximal direction. A central throughbore 86 of the end cap 36 receives the plunger rod 40. The throughbore 86 is sized to fit snugly over the porous seal 80. As seen in FIG. 4, the porous seal 80 fills the annular space between the piston rod 40 and the throughbore 86 of the end cap 36.

A safety seal 88 is provided for packaging and safe transport of the syringe 20 while carrying liquid. More particularly, the plunger 38 assumes a fully depressed position during transport with the stop ring 82 juxtaposed against the circular flange 84, as shown in FIG. 2b. The safety seal 88, which may be, for example, one-sided tape, is adhered around the junction of the stop ring 82 and flange 84. A perforated circle 90 is provided around the mid-portion of the safety seal 88. Upon first twisting and then moving of the plunger 38 in the direction of arrow 91 in FIG. 2c, the perforated circle 90 is ruptured allowing the syringe 20 to operate as desired. As indicated, the rupture of the perforated circle 90 may be facilitated by rotating the thumb ring 42 and integral stop ring 82 relative to the barrel 22.

Now looking at FIGS. 4 and 5, the outer barrel 22 includes a thickened region 92 adjacent the stem 30. The thickened, region 92 has an inner tapered surface 94. At the proximal end of, the region 92, a circular ledge 96 forms a contact and centering ring for the tubular guide 60. The annular space between the tubular guide 60 and the barrel 22 defines an outer fluid chamber or reservoir 98. The reservoir 98 serves as the primary receptacle for storing liquid medication, such as an anesthetic, or other fluid to be injected. However, due to the presence of the axial slots 68 and 76, fluid can freely pass between the reservoir 98 and a proximal portion 99 of the interior of the tubular element 62, although the syringe 20 is intended to function best with the majority of fluid remaining in the reservoir.

The resilient seal 70 on the distal end of the tubular element 62 has a forward taper 100 configured to seal against the tapered surface 94 of the barrel 22. As mentioned above, the tubular element 62 has an axial length such that it may move a short distance between the tapered surface 94 and the end cap 36 and within the confines of the guide 60.

The resilient seal 78 divides the inner volume of the tubular element 62 into a distal portion or delivery chamber 102 and the proximal portion 99. Thus, the delivery chamber 102 is in fluid communication with an ejection port 116 in the stem 30 when the tubular element 62 is in a distal position and the seal 70 is engaged with the tapered surface 94 as shown in FIG. 5. In this position, the seal 70 prevents fluid from passing between the reservoir 98 and the delivery chamber 102. The tubular element 62 may be displaced proximally into a second position shown in FIG. 4 wherein the seal 70 is disengaged from the tapered surface 94. In this second position, fluid may travel through a passageway 110 between the tapered surfaces 94 and 100. Thus, only when the tubular element 62 is slid into the second position can fluid travel from the reservoir 98 to the delivery chamber 102.

Assembly of the Syringe of FIG. 1

The present syringe 20 is designed to be filled with anesthetic or other fluid prior to final assembly and then transport to a hospital or medical facility for use. More particularly, the syringe 20 is assembled by first inserting the tubular guide 60 into the barrel 22 until the distal end contacts and seats on the circular ledge 96. Next, the tubular element 62 is slid within the guide 60. After assembling the porous seal 80 and end cap 36 over the stem 40, the plunger 38 is inserted into the tubular element 62, with resilient seal 78 being first placed into the tubular element. With the seal 70 of the element 62 pressed against the tapered surface 94, anesthetic or other fluid 106 is added to the reservoir 98 between the guide 60 and barrel 22. The disk portion 83 of the end cap 36 is then bonded to the proximal rim of the barrel 22. The means for bonding the cap 36 to the barrel 22 may be adhesion, heat seal, ultrasonic welding or other similar expedient. Finally, the plunger 38 is fully depressed so that the stop ring 82 comes into contact with the flange 84, whereupon the safety seal 88 is secured around the two components with the perforated circle 90 lined up in the junction plane.

The syringe 20 is then sealed from external contamination by the end cap 36, safety seal 88 and contact between seat 70 and tapered surface 94. A protective cap (not shown) may be attached over the stem 30 to prevent contamination in the ejection port 116.

Operation of the Syringe of FIG. 1

In order to use the syringe 20, the safety seal 88 is first ruptured at the perforated circle 90 by a twisting motion of the thumb ring 42 relative to the barrel 22, as seen in FIG. 2c. At this point, fluid 106 remains within the reservoir 98 by the contact between the seal 70 and tapered surface 94. Proximal movement of the plunger 38 as seen by arrow 108 creates friction between the resilient seal 78 and the inner surface of the tubular element 62. This friction causes the tubular element 62 to be displaced in a proximal direction, opening up the fluid passageway 110 between the seal 70 and tapered surface 94. After the tubular element 62 contacts the end cap 36, further movement of the plunger 38 creates a suction or reduced pressure in the delivery chamber 102. This suction pulls fluid 106 into the delivery chamber 102 from the reservoir 98. The fluid flow, as shown by arrows 112, passes through the axial slots 66, the fluid passageway 110 and orifice 72. During proximal movement of the plunger 38, air is introduced into the barrel 22 through the porous seal 80, as shown by arrows 114 in FIG. 4. The frictional surface contact with the flange 84 maintains the position of the porous seal 80 while allowing the plunger rod 40 to slide relative thereto.

When the delivery chamber 102 is filled, the medical technician bleeds any air therein and expels anesthetic through the ejection port 116 until the proper volume remains, as indicated by the graduation markings 74. in order to view fluid against the graduated markings 74, the barrel 22, tubular guide 60 and tubular element 62 are formed of transparent or translucent materials. After advancement of the needle 34 a first depth into the injection site 54, anesthetic is expelled though the ejection port 116 by distal movement of the plunger 38 via the thumb ring 42, as shown by movement arrow 56 in FIGS. 1a and 5. Initial distal movement of the plunger seal 78 urges the tubular element 62, and more specifically the seal 70, into engagement with the tapered surface 94 of the barrel 22. This closes off the fluid passageway 110 between the reservoir 98 and the delivery chamber 102. Further movement of the plunger 38 thus forces fluid from the delivery chamber 102 until the resilient seal 78 bottoms out against the inner surface of the seal 70.

After a first infusion of anesthetic at the first depth of the needle 34, the syringe 20 is advanced to position the needle at a second depth. At this point, the plunger 38 is again withdrawn relative to the barrel 22 via the thumb ring 42 and finger rest 46. After the frictional contact of the resilient seal 78 pulls the tubular element 62 against the end cap 36, and upon further proximal movement of the plunger 38, a negative pressure develops within the delivery chamber 102. Due to the proximal movement of the tubular element 62, the fluid passageway 110 is once again opened for anesthetic to flow along the path of arrows 112 in FIG. 4 through the orifice 72 and into the delivery chamber 102. In this manner the syringe 20 is once again primed and ready to deliver another infusion of anesthetic at the second needle depth.

This process can be repeated at successive depths until the injection site is sufficiently numbed, or until the anesthetic in the reservoir 98 is exhausted. The entire sequence of infusion-advance-prime-infusion can easily be accomplished with the thumb and fingers of only one hand. Furthermore, the priming and expulsion of fluid from the delivery chamber 102 is done by simply advancing and retracting the plunger 38 along the axis of the syringe 20.

Another benefit of the present syringe 20 is the large capacity of the reservoir 98 in combination with the relatively small force required to infuse fluid into the patient. More particularly, the inner diameter of the tubular element 62 is preferably between 1.0 and 1.5 cm. This small size enables the operator to generate a large pressure within the delivery chamber 102 with the application of only small forces on the thumb ring 42. At the same time, the barrel 22 may have an inner diameter of between 2 and 3 times the diameter of the tubular element 62, resulting in a large fluid storage capacity available to the delivery chamber 102. Conversely, the small diameter of the tubular element 62 also enables the operator to generate a large negative pressure in the delivery chamber 102 making it easy to prime the syringe 20 for another injection. In other words, it is easy to suck fluid into the delivery chamber 102. This helps reduce fatigue to the hands of the operator during a large number of repetitive injections.

The initial priming of the syringe 20 is preferably done external to the injection site 54. The protective cap (not shown) over the stem 30 seals the ejection port 116 to enable the plunger 38 to pull fluid into the deliver chamber 102 from the reservoir 98, rather than air in through the ejection port. After the needle 34 has been buried in the injection site 54, the small size of the needle orifice provides sufficient resistance to entry into the needle 34 of relatively viscous bodily fluids. The negative pressure required to pull fluid 106 into the delivery chamber 102 is primarily related to the resistance of air passage through the porous seal 80. Thus, the seal 80 is designed to exhibit less resistance to air passage than the resistance of the needle orifice to bodily fluids.

Dual-Chamber Syringe With Back-Flow Seal

As shown in FIG. 6, a second embodiment of a dual-chamber medical syringe 120 includes an outer tubular barrel 122 having a distal end 124 and a proximal end 126. The distal end 124 includes a tapered section 128 leading to a stem 130 for receiving a hub 132 of a needle 134. Again, the stem 130 is of a generally standard type in the medical industry, and various needles and the like will be readily received thereon.

The proximal end 126 of the barrel 122 is covered by a disk-shaped end cap 136 having an aperture 137 for receiving a plunger 138. The plunger 138 comprises a plunger rod 140 having a resilient plunger seal 142 fitted to a distal end, and a thumb ring 144 on its proximal end. The plunger rod 140 is sized to fit closely through the aperture 137, or a small gap may be provided for passage of a dose metering stick, as will be explained below. The barrel 122 further includes first and second pairs of outwardly extending finger rests 146 adjacent to the end cap 136, as well as a series of external circumferential grip ribs 148 formed on the barrel 122 between the finger rests. As with the first embodiment, the syringe 120 is configured to allow a medical technician to insert a thumb through the thumb ring 144 while gripping the barrel 122 with the index and middle fingers in the general location of the ribs 148. The syringe 120 exhibits proximal and distal finger rests 146 to allow an operator to displace the thumb ring 144, and associated plunger rod 140, in either axial direction with respect to the barrel 122.

Looking now at FIGS. 6 and 7, a channel member or tubular guide 150 concentrically fits within the tubular barrel 122. The guide 150 is tubular along its entire length until a distal taper 152 leading to a tubular neck 154. One or more axial slots 156 are formed along the neck 154 and extend to the distal tip abutting a thickened region 158 (FIG. 7) of the barrel 122. A resilient guide plug 159 is sized to engage firmly the solid portions in the distal tip of the neck 154 in advance of the slots 156, and is positioned so that liquid does not enter the interior of a tubular element 162 that receives the plunger 138. The proximal end of the tubular guide 150 contacts the end cap 136, and the distal end of the neck 154 abuts an annular surface 160 (FIG. 7) defined by a proximal face of the thickened region 158. The guide 150 is held in a fixed position within the barrel and is solid along its length except for the slots 156.

The tubular element 162 has a diameter slightly smaller than the tubular guide 150 and it includes a proximal tubular region and a tapered distal end 164 on which a needle or cannula 166 mounts. The cannula 166 extends distally to a tip 168. The tubular element 162 has an axial length from a proximal end 165 to the tapered end 164 shorter than the interior clearance within the tubular guide 150. The tubular element 162 can thus slide freely within the guide 150 between the end cap 136 and taper 152. in this respect, FIG. 6 illustrates the tubular element 162 in a first, proximal position within the guide 150 with the proximal end 165 abutting the end cap 136. FIG. 7 shows the element 162 in a second, distal position within the guide 150 with the tapered end 164 restricted by the taper 152. Preferably, the angles formed with the longitudinal axis by the taper 152 and tapered end 164 are identical. The plunger seal 142 forms a friction fit with the interior walls of the tubular element 162 such that movement of the plunger 138 displaces the tubular element 162 within the guide 150.

A back flow seal 170 firmly engages the interior walls of an ejection port 174 within the stem 130 of the barrel 122. In the first, proximal position of the tubular element 162, the tip 168 of the cannula 166 extends through the resilient guide plug 159 and into a refill space or chamber 172 formed between the back flow seal 170 and guide plug. In a second, distal position of the tubular element 162 the tip 168 of the cannula 166 extends through the back flow seal 170 and into the ejection port 174. The longitudinal movement of the tubular element 162 is caused by longitudinal movement of the plunger 138, as will be explained in more detail below.

FIG. 6 shows an intact safety seal 176 provided for packaging and safe transport of the syringe 120 while carrying liquid, while in FIG. 7 the seal 176 has been removed. The plunger 138 assumes a position during transport with a stop ring 178 held away from the end cap 136 by a cylindrical spacer 180 secured in position by the seal 176. The safety seal 176, which may be, for example, one sided tape, is adhered around the junction of the stop ring 178 and spacer 180. A pull tab is provided to remove the seal 176 and spacer 180, which is preferably constructed of thin plastic or other biocompatible material. The spacer 180 is designed to have sufficient column strength while supported by the outer seal 176 to prevent distal movement of the stop ring 178 toward the end cap 136 during shipping, yet be relatively fragile and easy to remove once the seal 176 has been peeled away in preparation for use of the syringe 120. Alternatively, the safety seal 176 itself may incorporate the spacer 180.

Operation of the Syringe With Back-Flow Seal

The syringe 120 holds an initial dose of medication such as, for example, insulin or anesthetic, within a delivery chamber 182 (FIG. 6) defined inside the tubular element 162 between the plunger seal 142 and the needle tip 168. The spacer 180 enables the plunger 138 to maintain this retracted position during shipping. After the seal 176 is removed, and the syringe needle 134 is positioned at a desired location in a patient, the plunger 138 may be actuated by the operator via the thumb ring 144, finger rests 146 and grip ribs 148 in the direction of arrow 184. Initial distal movement of the plunger 138 urges the tubular element 162 from its first, proximal position seen in FIG. 6 to the second, distal position of FIG. 7 by virtue of the friction between the plunger seal 142 and interior walls of the tubular element 162. Specifically, the tapered end 164 is displaced into engagement with the taper 152 of the guide 150. The needle tip 168 pierces the back flow seal 170 and enters the ejection port 174. Further movement of the plunger 138 forces fluid from the delivery chamber 182 until the plunger seal 142 bottoms out against the tapered end 164, or the stop ring 178 contacts the end cap 136. The fluid travels through the ejection port 174 as indicated by arrow 186 and is expelled from the needle 134.

The dual-chamber syringes of the present invention are especially suited for repeat injections at different depths, as indicated above. This is accomplished in the syringe 120 by storing a reserve supply of fluid in an outer reservoir 192 formed within the barrel 122 and outside of the tubular guide 150. The placement of the slots 156 is such to prevent communication between the reservoir 192 and interior of the tubular guide 150.

FIG. 8 illustrates the syringe 120 during retraction of the plunger 138 to refill the delivery chamber 182. Initial retraction of the thumb ring 144 in the direction of arrow 188 displaces the tubular element 162 from its second, distal position to its first, proximal position with the proximal end 165 abutting the end cap 136. The needle tip 168 is thus located within the refill chamber 172 in communication with the fluid in the reservoir 192. Further retraction of the plunger 138 creates a reduced pressure within the chamber 182 from the rearward movement of the plunger seal 142, drawing fluid into the tip 168, as indicated by arrows 194. The tubular element 162 may be calibrated to show the operator the volume of fluid therewithin, or a separate dose meter, described below, may be utilized to signal when a desired volume has been drawn into the delivery chamber 182. The process is repeated for as many times as necessary, or until the fluid within the reservoir 192 runs out, which lasts significantly longer than previous single-barrel syringes.

During the entire process, the cannula needle 168 remains centered by the resilient guide plug 159 to ensure repeated punctures through the center of the back flow seal 170. Additionally, the back flow seal 170 prevents fluid from being drawn into the syringe 120 through the injection needle 134 when the plunger 138 is being withdrawn to refill the delivery chamber 182.

Alternative Self-Locking Feature

FIG. 9 illustrates a syringe 200 which is similar in many respects to the syringe 20 of FIG. 1. An outer barrel 202 concentrically contains a tubular guide 204 having proximal slots 206, and a tube 208 capable of sliding axially therewithin. The tube 208 defines a valve 210 on a distal end having a central throughbore 212. A plunger 216 including a resilient member 218 on one end actuates the tube 208 axially within the guide 204 to open and close the valve 210, alternatively allowing and restricting fluid communication between an outer fluid reservoir and the interior of the tube 208. In a departure form the previous embodiment, an O-ring seal 214 is located within the space between the guide 204 and tube 208. The seal 214 prevents fluid from traveling proximally to an unsealed aperture 219 in an end cap 221 where the plunger 216 enters the syringe, thus preventing unwanted leakage therefrom. Additionally, the syringe 200 incorporates a safety seal 220 for shipping and stop ring 222, both of which are similar to those previously described with respect to FIG. 6. The plunger 216 additionally includes self-locking structure 224 which mates with locking tabs attached to the end cap 221 of the syringe 200. The specific locking structure will be more fully described and shown in detail below with respect to a further embodiment. The locking structure 224 more securely maintains the plunger 216 in its initial position during shipping, and in that respect supplements the safety seal 220.

Dual-Barrel Syringe With Automatic Dose Meter

FIG. 10 shows an intact dose meter 230 for use with any of the present dual-barrel syringes. The dose meter 230 enables the operator to automatically sense the correct dose when refilling the plunger delivery chamber without visual inspection. This is particularly Important when time is critical, and also when the doses are small, and manually metering the correct amount becomes more difficult.

The dose meter 230 comprises a split ring 232 forming nearly a complete circle and a calibrated stick 234. The stick 234 extends in an axial direction from a portion of the ring 232 opposite the split. As seen in FIG. 11, the calibrated stick 234 includes a plurality of identical calibrated segments 236 separated by weakened separation lines 238. The stick 234 may be shortened from an initial length by breaking off one or more segments 236 from the free end, as indicated in FIG. 11.

Figure 16:
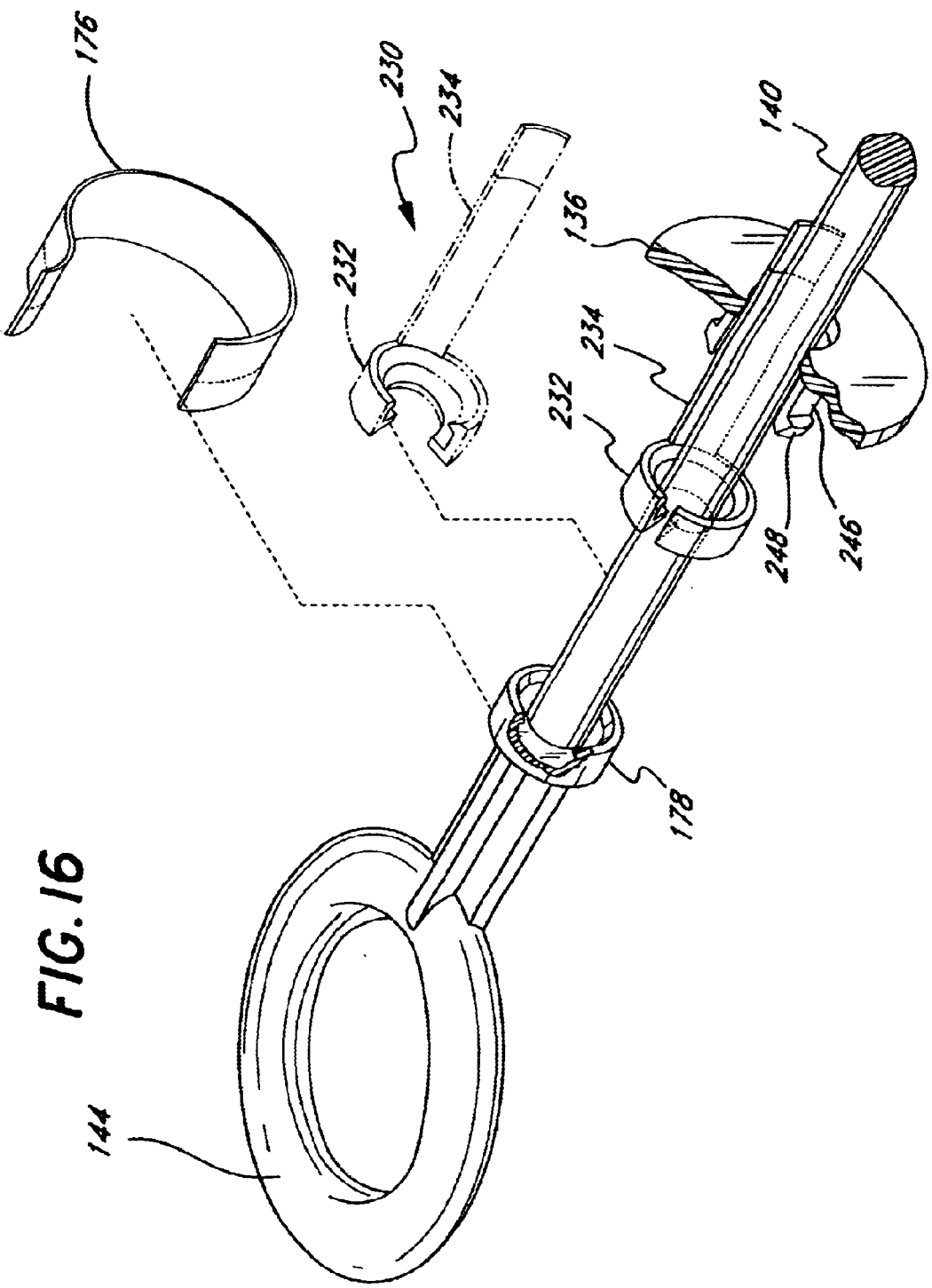
FIG. 16 is a detailed, exploded, perspective view of the proximal end of the syringe of FIG. 16 within the circle of FIG. 12 illustrating the placement of the dose meter.

FIGS. 12 and 16 show the placement of the dose meter 230 in relation to the dual-barrel syringe 120 of the present invention. After the aforementioned seal 176 has been removed and the plunger 138 retracted a short distance, the split ring 232 is spread apart to pass around and encircle the plunger stem 140. The calibrated stick 234 has an arcuate cross-section facilitating insertion into the small gap between the stem 140 and central aperture 137 through the end cap 136.

FIG. 13 shows the dose meter in an initial position prior to being affixed in place on the syringe 120. The split ring 230 includes a rib 242 extending radially inward from an outer wall portion 244. The end cap 136 includes a pair of axial fingers 246 (best seen in FIG. 16) diametrically opposed across the central aperture 137 and terminating in outward detents 248. The detents 248 are sized and shaped to interfere with the rib 242. The locking structure 224 mentioned above with reference to the embodiment of FIG. 9 is similar to the mating rib 242 and detents 248. The split ring 232, as well as the end cap 222 there, can be unlocked from the syringe by firm proximal movement to disengage the rib 242 and detents 248. In this respect, the fingers 246 are relatively thin so that any such cam action against the detents 248 bends the fingers fairly easily inwardly.

Figure 14:
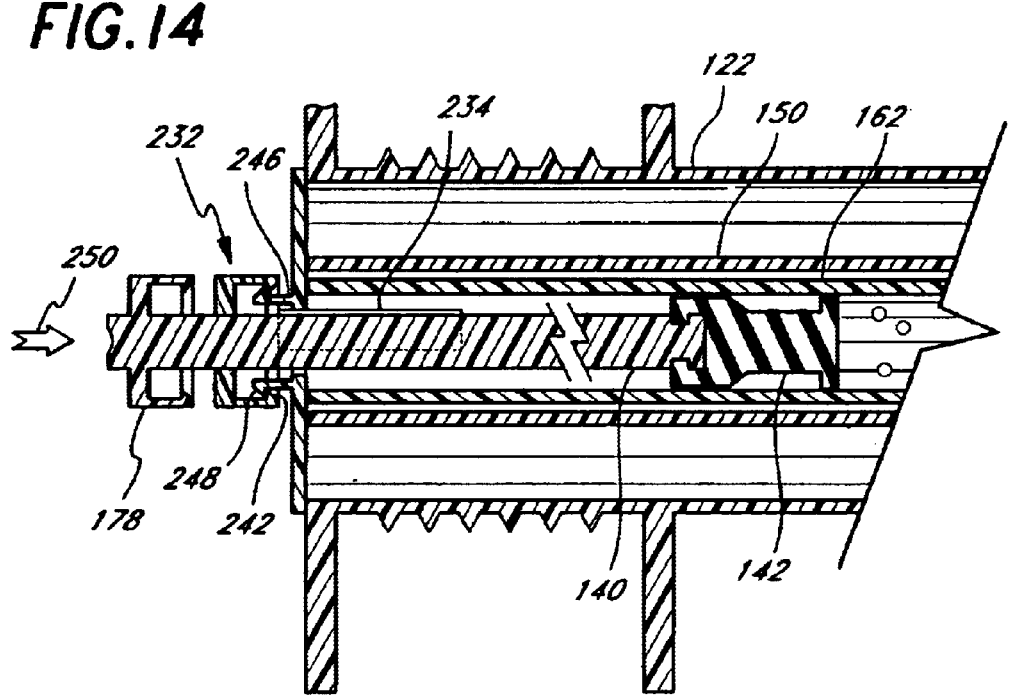
FIG. 14 is a detailed, cross-sectional view of the syringe of FIG. 12 during delivery of a fluid through an ejection port.
Figure 15:
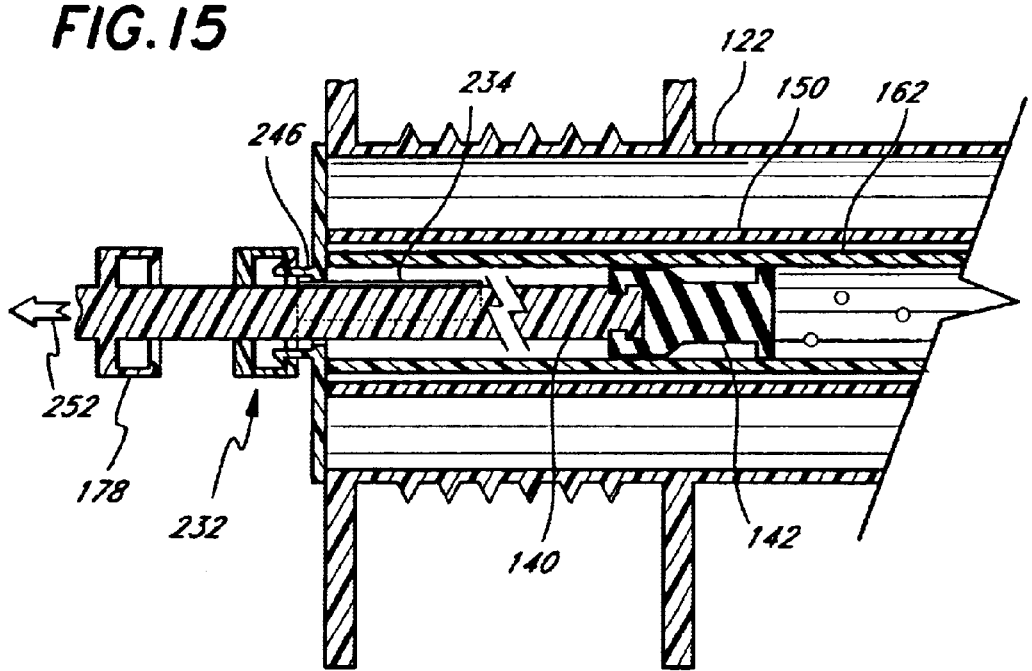
FIG. 15 is a detailed, cross-sectional view of the syringe of FIG. 12 during retraction of the plunger until restricted from further movement by the dose meter.

FIGS. 14 and 15 depict the use of the dose meter 230. Prior to use, the operator slides the split ring 232 distally to cam the rib 242 over the opposed detents 248. This can be accomplished during the initial delivery of fluid with the plunger 138, as indicated by the arrow 250 in FIG. 14. The dose meter 230 is thus held in a fixed axial location with respect to the end cap 136.

In the normal mode of operation, the dose meter 230 remains in place, with the unbroken portion of the calibrated stick 234 extending along the plunger stem 140 within the tubular element 162. Retraction of the plunger 138 in the direction of arrow 252 draws fluid into the delivery chamber 182, as mentioned previously. Because the concentric tubular members are transparent, volumetric markings 240 (FIG. 12) on the tubular element 162 may be visually monitored to determine the correct amount of fluid drawn therein. Preferably, however, the operator relies on the dose meter 230 to signal the when the correct dose has been drawn into the delivery chamber 182. Because the plunger seal 142 is not displaced with respect to the tubular element 162 until the proximal end 165 contacts the end cap, the movement of the plunger seal in drawing fluid can be measured relative to the dose meter 230 fixed with respect to the end cap 136. The stick 234 is calibrated to restrict the plunger seal 142 movement when a predetermined volume of fluid is drawn into the delivery chamber 182. Thus, as seen in FIG. 15, the plunger 138 cannot be retracted any farther, and a known quantity of fluid is temporarily stored in the delivery chamber 182. The fluid is then ejected from the syringe 120 and a new dose drawn into the delivery chamber 182 from the reservoir 192. This procedure can be repeated without the need of visually inspecting and estimating the volume of fluid within the tubular element 162. Such convenience is especially important when anesthetizing a deep area with a series of drug deliveries at successive depths. The dose meter 230 is thus a simple, reliable and accurate means for ensuring the correct amount of fluid is delivered for a succession of injections.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. For example, the outside of the syringe may be marked to indicate the amount of fluid injected into a patient; the reservoir may be divided into separate compartments, each holding one component of a two component medication system; and the reservoir may be charged with a gas to create positive pressure within the reservoir, eliminating the filter/seal. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the inventions

What is claimed is:

1. A medical syringe including
   a barrel with an ejection port at one end and a chamber holding a reservoir of liquid comprising,
   an internal partition member within said barrel that at least partially defines a channel terminating at the ejection port,
   a moveable tubular element seated within the channel and has an end nearby the injection port,
   a fluid passageway which allows the liquid to flow from the chamber into the tubular element, a plunger seated within the tubular element, having an end in the tubular element to which is attached a seal, said seal fitting snug against the tubular element to grip said tubular element and, in response to movement of the plunger, to move the tubular element between a first position where the injection port is sealed and the passageway is blocked to prevent liquid in the chamber from passing into the tubular element, and a second retracted position where the passageway is unblocked to allow liquid in the chamber to flow from the chamber through the passageway into the tubular member, said plunger as it is moved from the second retracted position towards the ejection port forcing any liquid in the tubular element out the injection port.

2. The medical syringe of claim 1 where there is an opening in the barrel having a porous seal which surrounds the plunger, said porous seal allowing air to enter the barrel yet inhibits the flow of liquid from the chamber.

3. The medical syringe of claim 1 where the plunger is initially in the first position and there is a safety seal on the plunger which is broken by movement of the plunger into the second retracted position.

4. The medical syringe of claim 1 where the chamber at least partially surrounds the channel.

5. The syringe of claim 1 where the amount of liquid drawn into the tubular element is limited by a dose meter.

* * * * *